United States Patent
Noguchi

(10) Patent No.: US 8,060,176 B2
(45) Date of Patent: Nov. 15, 2011

(54) LIVING BODY DATA DETECTOR

(75) Inventor: Eriko Noguchi, Chiba (JP)

(73) Assignee: Seiko Instruments Inc. (JP)

( * ) Notice: Subject to any disclaimer, the term of this patent is extended or adjusted under 35 U.S.C. 154(b) by 1100 days.

(21) Appl. No.: 11/895,492

(22) Filed: Aug. 23, 2007

(65) Prior Publication Data

US 2008/0058658 A1  Mar. 6, 2008

(30) Foreign Application Priority Data

Aug. 29, 2006  (JP) ................................ 2006-232187

(51) Int. Cl.
*A61B 5/0408* (2006.01)
(52) U.S. Cl. .................... 600/390; 600/386; 600/393
(58) Field of Classification Search .................. 600/386, 600/388–390, 393
See application file for complete search history.

(56) References Cited

U.S. PATENT DOCUMENTS

| 4,966,154 | A | 10/1990 | Cooper et al. |
| 5,353,793 | A * | 10/1994 | Bornn ............................ 600/386 |
| 5,491,474 | A | 2/1996 | Suni et al. ................. 340/870.31 |
| 5,564,429 | A | 10/1996 | Bornn et al. |
| 2002/0013538 | A1 | 1/2002 | Teller |
| 2008/0114232 | A1 | 5/2008 | Gazit ............................ 600/390 |

FOREIGN PATENT DOCUMENTS

| GB | 2 425 181 A | 10/2006 |
| JP | 57 29763 | 6/1982 |
| JP | 6245913 | 9/1994 |
| JP | 10155753 | 6/1998 |
| JP | 2003 220043 | 1/2002 |
| JP | 2002143140 | 5/2002 |

* cited by examiner

*Primary Examiner* — Lee Cohen
(74) *Attorney, Agent, or Firm* — Adams & Wilks

(57) ABSTRACT

A living body data detector equipped with a fitting belt which does not deviate in position, does not fall down and does not press the chest even when taking exercise while fitting it on is provided. A living body data detector comprises a fitting belt having a pair of shoulder belt portions that is, a left shoulder belt portion and a right shoulder belt portion, a pair of electrode portions attached to the fitting belt, and a living body signal detector portion connected to the pair of electrode portions through connection cables, and attached to the fitting belt. The left shoulder belt portion and the right shoulder belt portion are forming an intersected coupling portion on the back side of the user. A living body signal detector portion is attached to the intersected coupling portion. The left shoulder belt portion is provided with an expansion portion and a separable coupling means, and the right shoulder belt portion is provided with an expansion portion and a separable coupling means.

7 Claims, 3 Drawing Sheets

US 8,060,176 B2

LIVING BODY DATA DETECTOR

BACKGROUND OF THE INVENTION

1. Field of the Invention

This invention relates to a living body data detector including a detector circuit that detects living body signals by processing signals generating across a pair of electrodes attached to a fitting belt, and a transmitter circuit for transmitting the living body signal data. The living body data detector constitutes a living body data measuring device together with a living body data display which displays the living body data upon receiving the living body signal data.

2. Description of the Related Art

A heart beat measuring instrument is a representative example of the living body data measuring device, and is, usually, constituted by a heart beat detector having a detector circuit for detecting heart beat signals by processing a cardiac potential generating across a pair of chest electrodes attached to a chest belt and a radio transmitter circuit for transmitting the heart beat signals, and a wristwatch type electronic timepiece including a radio receiver unit for receiving the heart beat signals, a heart beat operation circuit for calculating the heart rate by processing the heart beat signals, and a display circuit for displaying the heart rate.

Heart beat measuring instruments equipped with a chest belt have been disclosed in JP-A-6-245913, JP-A-2002-143110, JP-A-10-155753 and U.S. Pat. No. 5,491,474.

In these conventional heart beat measuring instruments, the chest belt itself has a width wider than that of a trouser belt but basically has the same structure. However, despite its decreased size and reduced weight, the heart beat measuring instrument mounted on the chest belt has a weight comparable to about that of a general wristwatch body. This is because the heart beat measuring instrument is constituted by having various electronic parts, a mechanical part, a cell and a casing for holding them. Therefore, when the conventional heart beat measuring instrument equipped with the chest belt is fitted to the human body, the position tended to be deviated due to the weight of the heart beat measuring instrument.

If it is attempted to prevent the deviation in position, the length-adjusting means must be operated to strongly fasten the chest belt so as to be fitted to the human body. However, the chest belt that is fitted by being strongly tightened presses the chest of the user causing such a problem that upon wearing the belt the user finds it uncomfortable being pressed and uneasy to breath. Another problem is that the electrode portions for detecting the cardiac potential must be brought into direct contact with the human body, and the living body data detector such as the heart beat measuring instrument that uses the chest belt must be fitted prior to wearing the clothing.

SUMMARY OF THE INVENTION

A first object to be solved by the invention is to provide a living body data detector which does not cause the fitting belt to be deviated in position or fall down even when taking exercise. A second object to be solved by the invention is to provide a living body data detector equipped with a fitting belt which does not deviate in position, does not fall down and does not press the chest even when taking exercise.

In order to solve the above first object, a living body data detector comprises a fitting belt having a left shoulder belt portion and a right shoulder belt portion, a pair of electrode portions attached to the left shoulder belt portion and to the right shoulder belt portion, and a living body signal detector portion electrically connected to the pair of electrode portions and attached to the fitting belt. In order to solve the above second object, a living body data detector comprises an expansible fitting belt having a left shoulder belt portion and a right shoulder belt portion, a pair of electrode portions attached to the left shoulder belt portion and to the right shoulder belt portion, and a living body signal detector portion electrically connected to the pair of electrode portions and attached to the fitting belt.

This invention is concerned with a living body data detector having a fitting belt which is worn upon passing the arms through the pair of right and left shoulder belt portions, eliminating the probability of deviation in position of the fitting belt or falling thereof even when taking exercise while fitting it on. Further, the living body data detector according to the invention has a fitting belt which is worn upon passing the arms through the pair of right and left shoulder belt portions, and forms an intersection portion at the back when fitted providing close contact between the electrode portions and the human body. In the present invention, the fitting belt is constituted by an expansible belt causing no pressure on the chest when it is fitted and liberating the user from finding it uneasy to breath when the belt is fitted. Further, the user who is wearing a sleeveless running shirt is allowed to wear the living body data detector of the invention without the need of taking the running shirt off. Further, the fitting belt corrects the posture in a direction in which the line of the backbone is straightened. Therefore, the user who wears the living body data detector of the invention is allowed to take exercise such as running or the like maintaining good posture.

DESCRIPTION OF THE PREFERRED EMBODIMENTS

The living body data detector according to the invention comprises an expansible fitting belt having a left shoulder belt portion and a right shoulder belt portion, a pair of electrode portions attached to the left shoulder belt portion and to the right shoulder belt portion, and a living body signal detector portion electrically connected to the pair of electrode portions and attached to the fitting belt.

Embodiment 1

Figure 1:
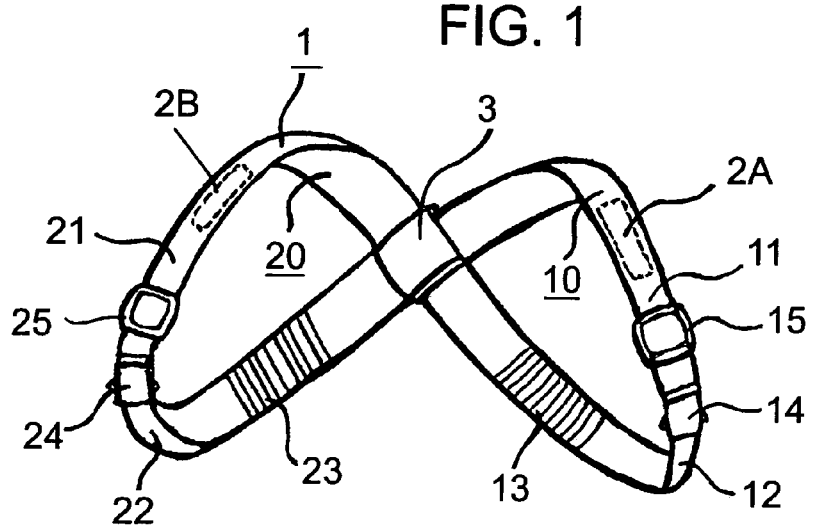
FIG. 1 is a perspective view of a living body data detector according to an embodiment 1 of the invention.
Figure 2:
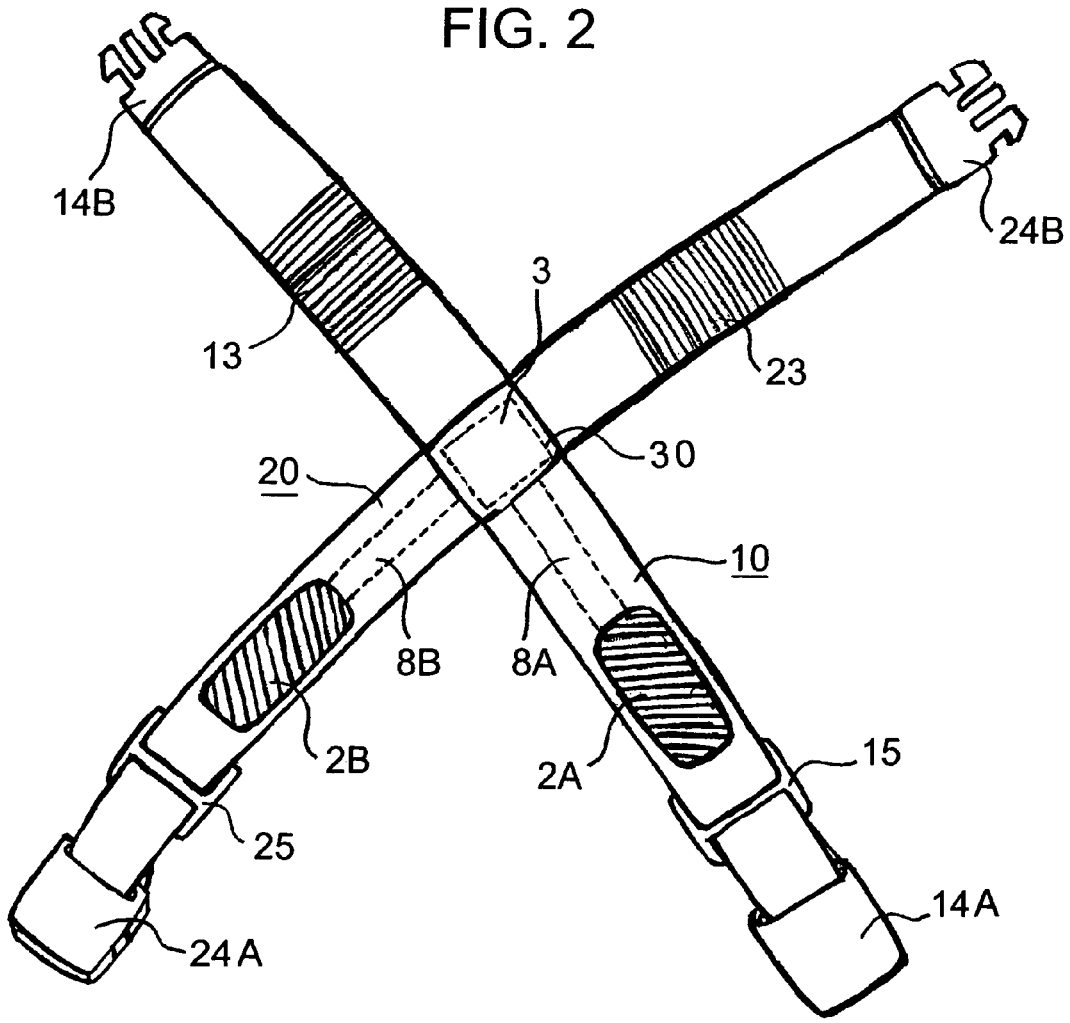
FIG. 2 is a back view of the living body data detector according to the embodiment 1 of the invention.
Figure 3A:
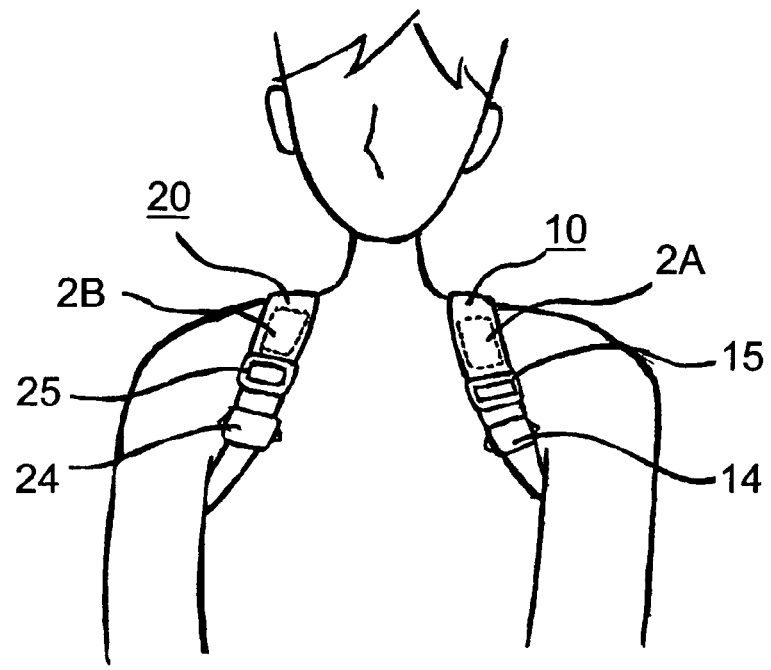
FIG. 3 includes a front view (A) and a back view (B) illustrating a state where the living body data detector of the embodiment 1 of the invention is fitted.
Figure 3B:
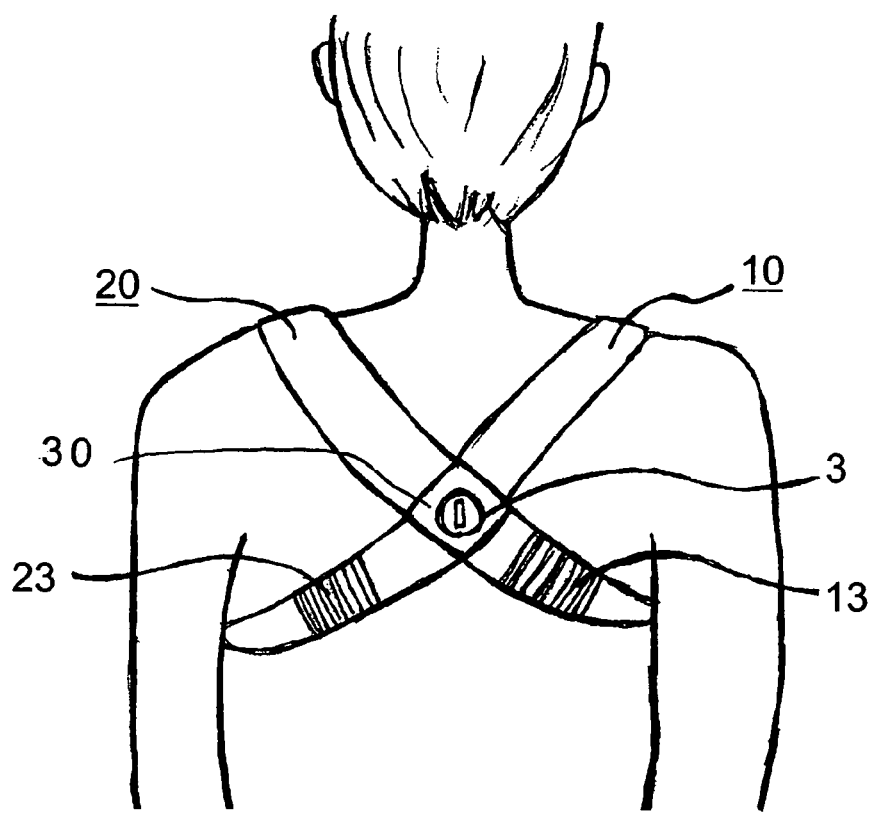

As shown in a perspective view of FIG. 1, a back view of FIG. 2, and a front view (a) and a back view (b) illustrating the fitted state of FIG. 3, the living body data detector according to an embodiment 1 of the invention is a heart beat measuring instrument which comprises a fitting belt 1 having a pair of shoulder belt portions including a left shoulder belt portion 10 and a right shoulder belt portion 20, a pair of electrode portions 2A and 2B attached to the fitting belt 1, and a living body signal detector portion 3 connected to the pair of electrode portions 2A and 2B through connection cables 8A and 8B, and attached to the fitting belt 1.

When the fitting belt 1 is fitted, a position where the electrode portion 2A is attached is a portion of the left chest between the armpit and the shoulder on the left side of the user or, in other words, a belt portion where the electrode portion 2A comes in contact with a portion of the left chest near the root of the left arm. Similarly, when the fitting belt 1 is fitted, a position where the electrode portion 2B is attached is a portion of the right chest between the armpit and the shoulder on the right side of the user or, in other words, a belt portion where the electrode portion 2B comes in contact with a portion of the right chest near the root of the right arm.

The left shoulder belt portion 10 has a shoulder pad belt portion 11 and an armpit pad belt portion 12 which are coupled together at the ends on one side thereof by separable coupling means 14 on the chest side of the user. The right shoulder belt portion 20 has a shoulder pad belt portion 21 and an armpit pad belt portion 22 which are coupled together at the ends on one side thereof by separable coupling means 24 on the chest side of the user. The ends at the other side of the shoulder pad belt portion 11 and the armpit pad belt portion 12 of the left shoulder belt portion 10 are coupled to the ends on the other side of the shoulder pad belt portion 21 and the armpit pad belt portion 22 of the right shoulder belt portion 20 on the back side of the user to form an intersected coupling portion 30.

The fitting belt 1 is provided with expansion portions 13 and 23 constituted by a rubber belt or a cloth belt in which rubber yarns are sewn to impart a suitable degree of expansion property and to maintain an optimum state of fitting. The expansion portion 13 is provided in the armpit pad belt portion 12 of the left shoulder belt portion 10, and the expansion portion 23 is provided in the armpit pad belt portion 22 of the right shoulder belt portion 20.

The separable coupling means 14 is a generally employed part such as a buckle constituted by a socket 14A and a plug 14B. The socket 14A and the plug 14B are fixed to the ends of the shoulder pad belt portion 11 and of the armpit pad belt portion 12 of the left shoulder belt portion 10. Similarly, the separable coupling means 24 is a generally employed part such as a buckle constituted by a socket 24A and a plug 24B. The socket 24A and the plug 24B are fixed to the ends of the shoulder pad belt portion 21 and of the armpit pad belt portion 22 of the right shoulder belt portion 20.

The length-adjusting means 15 of the left shoulder belt portion 10 is provided near the socket 14A of the shoulder pad belt portion 11. Further, the length-adjusting means 25 of the right shoulder belt portion 20 is provided near the socket 24A of the shoulder pad belt portion 21. The length-adjusting means 15 as well as the length-adjusting means 25, too, are generally employed parts used for adjusting the length of the belt.

The living body signal detector portion 3 is provided on the front side of the intersected coupling portion 30. The intersected coupling portion 30 is shown as a rectangle of a side equal to the belt width, but may be of a circular shape or an elliptic shape. In effect, the intersected coupling portion 30 may have an area large enough for mounting the living body signal detector portion 2.

Embodiment 2

Figure 4:
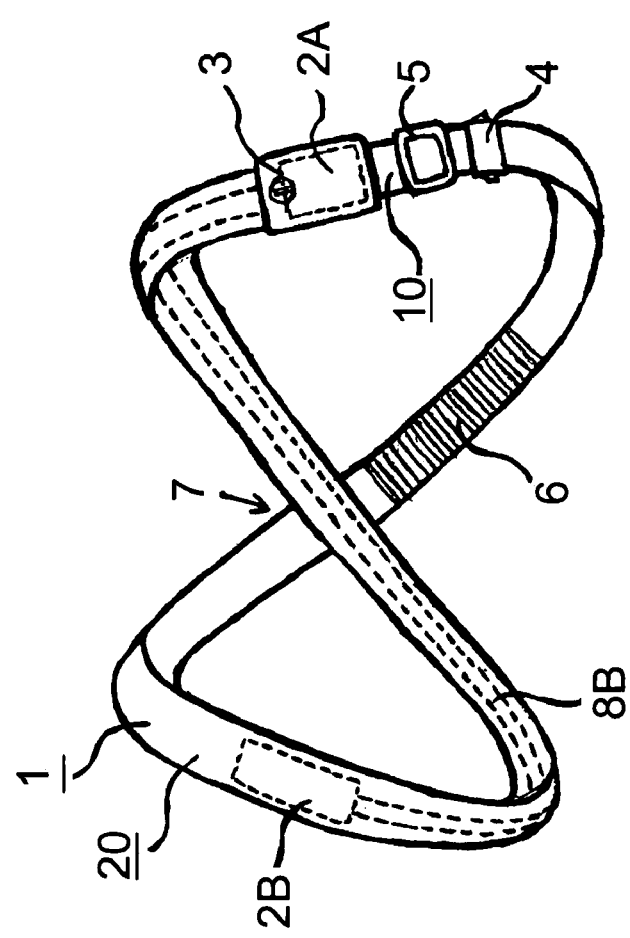
FIG. 4 is a perspective view of the living body data detector according to an embodiment 2 of the invention.
Figure 5:
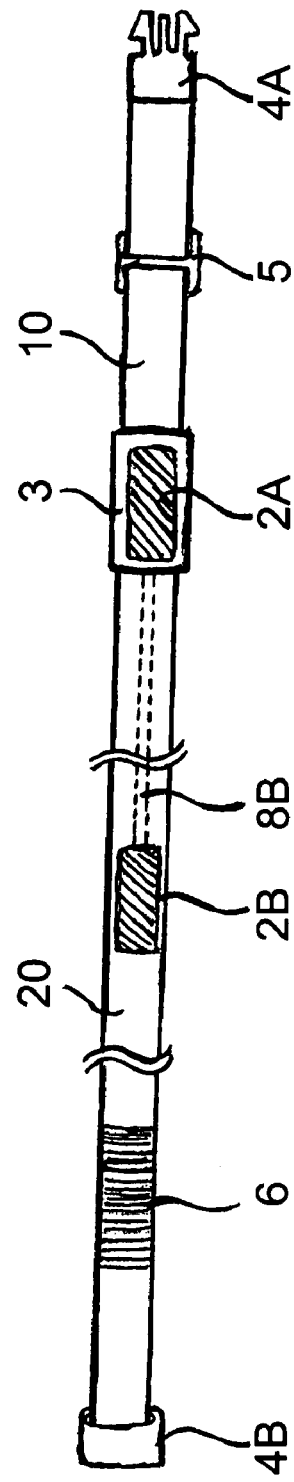
FIG. 5 is a back view of the living body data detector according to the embodiment 2 of the invention.

As shown in a perspective view of FIG. 4 and a back view of FIG. 5, the living body data detector according to an embodiment 2 of the invention is a heart beat measuring instrument which comprises the fitting belt 1 that includes the left shoulder belt portion 10 and the right shoulder belt portion 20 which are coupled together by a separable coupling means 4, and is fitted to the human body forming a ring in a coupled state and forming a crossed intersection portion 7 on the back side; a pair of electrode portions 2A and 2B attached to the fitting belt 1; and a living body signal detector portion 3 attached to the fitting belt 1.

The position where the living body signal detector portion 3 is attached to the fitting belt 1 is the same as the position of attaching the electrode portion 2A. That is, the electrode portion 2A is attached to the back side of the left shoulder belt portion 10 of the fitting belt 1 at the position where the electrode is attached, and the living body signal detector portion 3 is attached to the front side of the left shoulder belt portion 10 of the fitting belt 1 at the position where the electrode is attached. When the fitting belt 1 is fitted, the position of attaching the electrode portion 2A is a portion of the left chest between the armpit and the shoulder on the left side of the user or, in other words, a belt portion that comes in contact with a portion of the left chest near the root of the left arm. Similarly, when the fitting belt 1 is fitted, the position of attaching the electrode portion 2B is a portion of the right chest between the armpit and the shoulder on the right side of the user or, in other words, a belt portion that comes in contact with a portion of the right chest near the root of the right arm.

To fit the fitting belt 1, both ends thereof are fixed by using the separable coupling means 4 to form a loop which is, then, twisted like a figure eight as shown in FIG. 4, and the arms are passed through the right and left two loops such that the crossed intersection portion 7 is positioned on the back. Namely, the fitting belt 1 of the embodiment 2 is fitted in a manner of being tucked up.

The living body signal detector portion 3 is connected to the one electrode portion 2A via the connection cable SA and is further connected to the other electrode 2B via another connection cable that is not shown. The connection cable SA is buried in the armpit pad belt portion 22 of the right shoulder belt portion 20 and in the shoulder pad belt portion 21 of the right shoulder belt portion 20.

The fitting belt 1 is provided with an expansion portion 6 constituted by a rubber belt or a cloth belt in which rubber yarns are sewn to impart a suitable degree of expansion property and to maintain an optimum state of fitting. The expansion portion 6 is provided in the armpit pad belt portion 12 of the left shoulder belt portion 10 or in the shoulder pad belt portion 21 of the right shoulder belt portion 20.

The separable coupling means 4 is a generally employed removable coupling part such as a buckle constituted by a socket 4A and a plug 4B. The socket 4A and the plug 4B are fixed to the ends of the fitting belt 1. The length-adjusting means 5 of the fitting belt 1 is provided between the electrode portion 2A and the insertion fitting 4B.

What is claimed is:
1. A living body data detector comprising: a fitting belt having a left shoulder belt portion and a right shoulder belt portion; two electrode portions respectively attached to the left shoulder belt portion and to the right shoulder belt portion; and a living body signal detector portion electrically connected to the pair of electrode portions and attached to the fitting belt, wherein
the left shoulder belt portion has a shoulder pad belt portion and an armpit pad belt portion which are coupled together at the ends on one side thereof by separable coupling means on the chest side;
the right shoulder belt portion has a shoulder pad belt portion and an armpit pad belt portion which are coupled together at the ends on one side thereof by separable coupling means on the chest side:

the ends at the other side of the shoulder pad belt portion and the armpit pad belt portion of the left shoulder belt portion are coupled to the ends on the other side of the shoulder pad belt portion and the armpit pad belt portion of the right shoulder belt portion on the back side to form a belt-coupling portion;

the two electrode portions are attached to the shoulder pad belt portions of the left shoulder belt portion and the right shoulder belt portion on the chest side; and the living body signal detector portion is attached to belt-coupling portion.

2. The living body data detector according to claim 1; wherein expansion portions are provided for the armpit pad belt portions of the left shoulder belt portion and the right shoulder belt portion.

3. The living body data detector according to claim 1; wherein length-adjusting means are provided for the shoulder pad belt portions of the left shoulder belt portion and the right shoulder belt portion for adjusting the lengths thereof.

4. A living body data detector comprising: a fitting belt having a left shoulder belt portion and a right shoulder belt portion; two electrode portions respectively attached to the left shoulder belt portion and to the right shoulder belt portion; and a living body signal detector portion electrically connected to the pair of electrode portions and attached to the fitting belt, wherein the fitting belt includes the left shoulder belt portion and the right shoulder belt portion which are coupled together by a separable coupling means, and is fitted to the human body forming a ring in a coupled state and forming a crossed belt intersection portion on the back side;

the two electrode portions are attached to the shoulder pad belt portions of the left shoulder belt portion and the right shoulder portion on the chest side; and the living body signal detector portion is attached to either one of the two electrode portions on the front side.

5. The living body data detector according to claim 4; wherein the separable coupling means is provided for the shoulder pad belt portion of either the left shoulder belt portion or the right shoulder belt portion.

6. The living body data detector according to claim 4; wherein an expansion portion is provided for the shoulder pad belt portion of either the left shoulder belt portion or the right shoulder belt portion.

7. The living body data detector according to claim 4; wherein length-adjusting means is provided near the separable coupling means for adjusting the length of the fitting belt.

* * * * *